US009713459B2

(12) United States Patent
Mattrey et al.

(10) Patent No.: US 9,713,459 B2
(45) Date of Patent: Jul. 25, 2017

(54) METHOD AND SYSTEM FOR IN VIVO HYDROGEN PEROXIDE DETECTION WITH ULTRASOUND

(71) Applicant: The Regents of the University of California, Oakland, CA (US)

(72) Inventors: Robert Mattrey, San Diego, CA (US); Zhe Wu, San Diego, CA (US); Emilia Olson, La Jolla, CA (US); Joseph Wang, San Diego, CA (US); Wei Gao, La Jolla, CA (US); Christopher D. Malone, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 65 days.

(21) Appl. No.: 14/407,450

(22) PCT Filed: Jun. 11, 2013

(86) PCT No.: PCT/US2013/045274
§ 371 (c)(1),
(2) Date: Dec. 11, 2014

(87) PCT Pub. No.: WO2013/188470
PCT Pub. Date: Dec. 19, 2013

(65) Prior Publication Data
US 2015/0148667 A1    May 28, 2015

Related U.S. Application Data

(60) Provisional application No. 61/658,325, filed on Jun. 11, 2012.

(51) Int. Cl.
*A61B 5/05* (2006.01)
*A61B 8/08* (2006.01)
(Continued)

(52) U.S. Cl.
CPC ............ *A61B 8/481* (2013.01); *A61B 8/0841* (2013.01); *A61B 8/4483* (2013.01); *A61B 90/39* (2016.02);
(Continued)

(58) Field of Classification Search
CPC .......... A61B 2090/3925; A61B 8/0841; A61B 8/4483; A61B 8/481; A61B 90/39
See application file for complete search history.

(56) References Cited

U.S. PATENT DOCUMENTS

| 4,340,448 A | 7/1982 | Schiller et al. |
| 5,558,094 A | 9/1996 | Quay |

(Continued)

FOREIGN PATENT DOCUMENTS

| EA | 9836 B1 | 4/2008 |
| RU | 2016901 C1 | 7/1994 |

(Continued)

OTHER PUBLICATIONS

Turrens et al, Protection against Oxygen Toxicity by Intravenous Injection of Liposome-entraped Catalase and Superoxide Dismutase, J. Clin. Invest., vol. 73, Jan. 1984, pp. 87-95.*

(Continued)

*Primary Examiner* — Jonathan Cwern
*Assistant Examiner* — Amelie R Gillman
(74) *Attorney, Agent, or Firm* — Eleanor Musick; Musick Davison LLP

(57) ABSTRACT

A method and system are provided for detection of localized hydrogen peroxide within tissue by introducing a catalase-containing material into at location of interest, positioning an ultrasound transducer over the location, and generating an ultrasound image to detect microbubbles, where the presence of microbubbles indicate the presence of localized hydrogen peroxide. The catalase-coated surface may be the (Continued)

inner surface of a microtube, on the surface of or incorporated within a nanosphere or microsphere, or an implantable device.

28 Claims, 14 Drawing Sheets

(51) Int. Cl.
    *A61K 49/22*     (2006.01)
    *A61B 8/00*     (2006.01)
    *A61F 2/00*     (2006.01)
    *A61F 2/02*     (2006.01)
    *A61M 25/01*     (2006.01)
    *A61B 90/00*     (2016.01)

(52) U.S. Cl.
    CPC .............. *A61F 2/0063* (2013.01); *A61F 2/02* (2013.01); *A61K 49/223* (2013.01); *A61K 49/225* (2013.01); *A61M 25/0108* (2013.01); *A61B 2090/3925* (2016.02); *A61F 2250/0096* (2013.01)

(56) References Cited

U.S. PATENT DOCUMENTS

| | | | | |
|---|---|---|---|---|
| 5,991,650 | A * | 11/1999 | Swanson .............. | A61B 5/0422 374/E1.005 |
| 2003/0054027 | A1 * | 3/2003 | Unger ................ | A61K 41/0028 424/450 |
| 2004/0241202 | A1 * | 12/2004 | Chluba ................ | A61K 9/209 424/423 |
| 2005/0079201 | A1 | 4/2005 | Rathenow et al. | |
| 2005/0266086 | A1 * | 12/2005 | Sawhney ............. | A61K 31/765 424/486 |
| 2007/0055326 | A1 * | 3/2007 | Farley ................... | A61B 18/08 607/96 |
| 2007/0154466 | A1 * | 7/2007 | Weber ................. | A61K 31/727 424/94.4 |
| 2011/0236320 | A1 | 9/2011 | Schneider et al. | |

FOREIGN PATENT DOCUMENTS

| | | |
|---|---|---|
| RU | 2022016 C1 | 10/1994 |
| RU | 2114637 C1 | 10/1998 |
| RU | 2345793 C2 | 2/2009 |

OTHER PUBLICATIONS

Gao et al, Polymer-based tubular microbots: role of composition and preparation, Nanoscale, 2012, 4, pp. 2447-2453.*
Qi et al, Preparation and Characterization of Catalase-Loaded Solid Lipid Nanoparticles Protecting Enzyme against Proteolysis, Int J Mol Sci. 2011, 12(7), pp. 4282-4293.*
Wang, Mesoporous Silica Spheres as Supports for Enzyme Immobilization and Encapsulation, Chem. Mater. 2005, 17, pp. 953-961.*
Halliwell et al, Hydrogen peroxide in the human body, FEBS Letters 486 (2000), pp. 10-13.*
Perng et al.,"Ultrasound Imaging of Oxidative Stress In Vivo with Chemically-Generated Gas Microbubbles," Ann Biomed Eng (2012) 40:2059-2068.*
Yang et al., "A Hydrogen Peroxide-Responsive O2 Nanogenerator for Ultrasound and Magnetic-Resonance Dual Modality Imaging," Adv. Mater. (2012)24:5205-5211.*
International Search Report and Written Opinion for PCT/US2013/045274, mailed on Oct. 24, 2013, 8 pages.

* cited by examiner

FIG. 2A
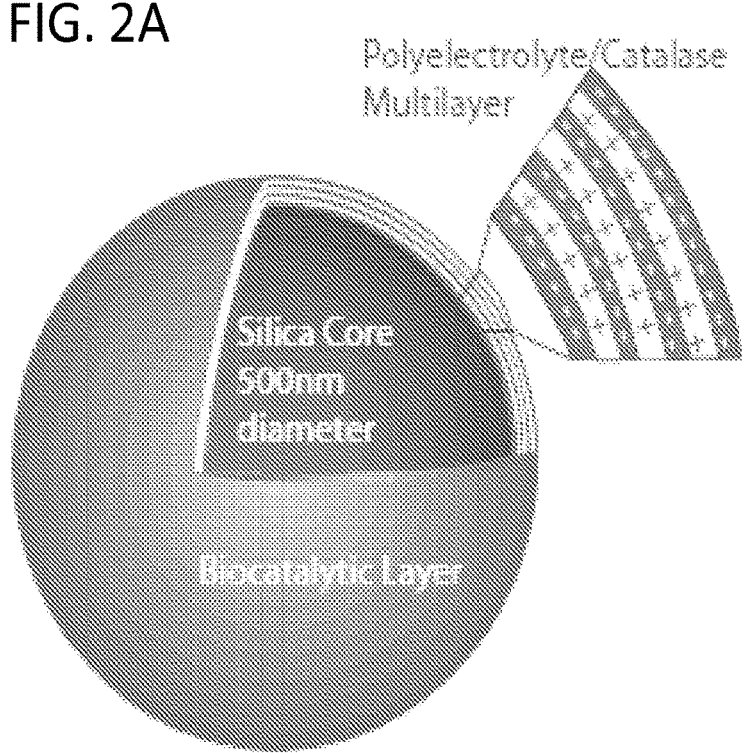
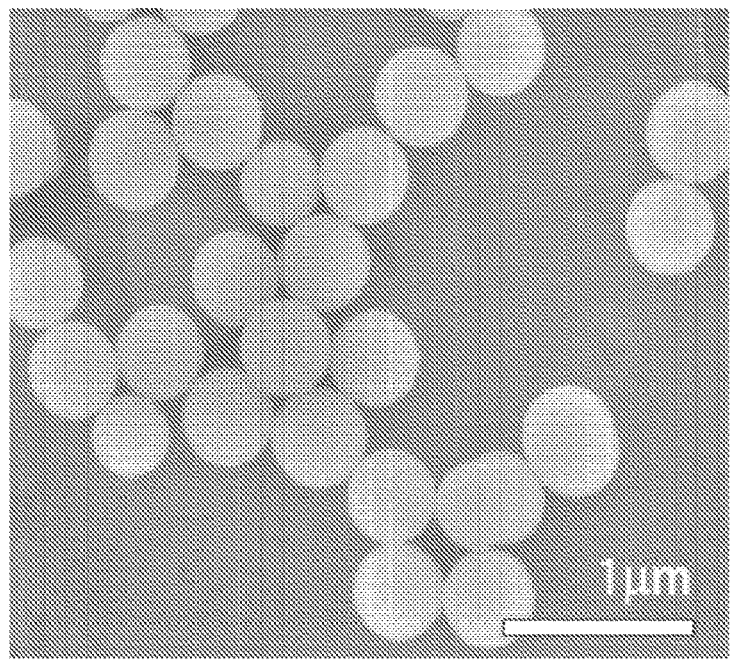
FIG. 2B

METHOD AND SYSTEM FOR IN VIVO HYDROGEN PEROXIDE DETECTION WITH ULTRASOUND

RELATED APPLICATIONS

This application is a '371 national stage filing of International Application No. PCT/US2013/045274, filed Jun. 11, 2013, which claims the benefit of the priority of U.S. Provisional Application No. 61/658,325, filed Jun. 11, 2012, which are incorporated herein by reference in their entirety.

FIELD OF THE INVENTION

The present invention relates to a method for detecting of biological processes, and more particularly to the detection of oxygen bubbles produced by hydrogen peroxide using ultrasound imaging.

BACKGROUND OF THE INVENTION

Infection is a common source of morbidity in hospitalized patients, many of whom have multiple venous lines, catheters, or other implantable devices in place for extended periods of time. For example, catheter-associated infections represent up to 80% of urinary tract infections in hospitalized patients, yet there is currently no means for detecting whether such an infection exists until the infection has progressed.

Existing practices for management of catheters in a clinical setting rely primarily on statistically-determined guidelines. For example, guidelines state that postoperative urinary catheters should be removed 48 hours post operatively. Additional guidelines exist for treatment of select populations with prophylactic antibiotics. If patient behavior suggests a potential infection, for example, inability to void, fever, etc., a dipstick and urinary analysis is performed. Similarly, if a central line infection is suspected, two sets of blood cultures are typically taken for culture. Urinalysis results can usually be obtained in one to two hours, while urine and blood culture results usually being returned in one to two days. In addition to the disadvantages of the relatively long turnaround time, these tests have a relatively high false positive rate and result in many patients being placed on antibiotics unnecessarily.

Hydrogen peroxide ($H_2O_2$) is a toxic byproduct of many physiologic reactions, formed either directly or by enzymes to consume the harmful oxygen free radicals produced during oxidative metabolism. Tissues have evolved sophisticated pathways to control $H_2O_2$, using it at low levels for intracellular signaling (<20 µM), at high levels by itself or converted to more harmful oxides for defense (>50 µM), or catalyze it into $O_2$ and water by the enzyme catalase to protect themselves. An imbalance results in elevated levels and is seen in oxidative stress, inflammation, and aging. Hydrogen peroxide is also involved in cancer, diabetes, neurodegeneration, acute respiratory distress (ARDS), and cardiovascular disease. As such, it has potential use for localized detection of a wide variety of biochemical processes in vivo. However, to date, most methods for detecting $H_2O_2$ have been confined to in vitro diagnostic use. Prototypes for a few specialized fluorescence, magnetic resonance and genetically encoded probes have been reported, but there is currently no robust injectable probe that can detect $H_2O_2$ to localize regions with elevated levels of $H_2O_2$ such as areas of inflammation, etc. in humans.

Existing methods include horseradish peroxidase with artificial substrates, which provides high sensitivity in vitro; ferrous oxidation in the presence of xylenol orange; genetically encoded probes such as those incorporating a substrate of SNAP-tag; roGFP or Hyper; MR contrast agents capable of detecting $H_2O_2$; enzyme electrodes (such as silica nanowire sensors); (13)C-Benzoylformic acid detection using specialized C-13 hyperpolarized MR sequences; and chemiluminescent nanoparticles.

Currently, detection in collected or voided fluids is compromised by autoxidation when exposed to atmospheric $pO_2$, causing artificial increases in $H_2O_2$ levels and decreased accuracy. Fluorescence-based assays, such as Amplex Red or ferrous oxidation of xylenol orange (FOX), are susceptible to contamination by other urine or plasma constituents and are not routinely available in clinical laboratories. Electrochemical and optical-based probes have been developed but are expensive and more difficult to incorporate into routine devices or standard clinical protocols to be practical.

Results have been reported on detection of implant-associated neutrophil responses using a nanoprobe targeting the formyl peptide receptor, however, this is an optical reporter and its clinical use is limited by overlying tissue thickness.

Another technology makes use of increased turbidity detectable in a discharge fluid from an infected catheter tube. The approach also relies on optical imaging and is likely to generate anomalous results in bloody fluids. In other developments, sensors have been designed to monitor the pH of biofilm-producing organisms such as Proteus bacilli, however, these are specific to a single organism.

In view of the foregoing, the need remains for a simple and low cost sensor for monitoring oxidative stress that can be incorporated into existing indwelling devices such as Foley or central venous catheters as a means for detecting $H_2O_2$ in real time using conventional clinical instrumentation.

SUMMARY OF THE INVENTION

Recent advances in chemically-powered synthetic nanomotors have made these devices promising tools for addressing many biomedical challenges. These catalytic nanoconverters have been used to isolate molecular oxygen that either dissolves or takes the form of microbubbles at sufficiently high (0.2%) fuel concentration. Ultrasound is a widely used clinical imaging modality with high sensitivity to gas-liquid interfaces such as microbubbles. The detection of these microbubbles relies on their non-linear oscillations distinguishing them from background tissue and provides the basis of contrast-enhanced ultrasonography.

The present invention employs an ultrasound (US) molecular imaging approach involving the productions of microbubbles (MBs) in situ. Catalytic nanoconverting materials are used to produce microbubbles that can be detected at lower concentrations of $H_2O_2$ using ultrasound. Neutrophils are the hallmark of acute inflammation. Since $H_2O_2$ is produced in 60-100 µM quantities by activated neutrophils in inflammatory tissues, the MBs may be used to detect infections or other diseases associated with elevated level of $H_2O_2$ such as cancer or ischemic injury, etc. Additional applications of the inventive method include visualization of metabolites or other reactive oxygen species that can be converted to hydrogen peroxide, and fueling oxygen requirements for physiologic reactions.

In one aspect of the invention, a method is provided for detection of localized hydrogen peroxide, including introducing a catalase material into a location of interest; positioning an ultrasound transducer over the location of interest; and generating and detecting an ultrasound signal to generate an image therefrom, wherein the presence of microbubbles within the image indicates the presence of localized $H_2O_2$. In one embodiment, the location of interest may be a fluid extracted from a patient such as urine, pus, or liquid removed from a mass. In another embodiment, the location of interest is tissues, where the catalase-containing material may be introduced into the tissue percutaneously, by inserting the device through a body orifice, such as the urethra, or by intravenous injection or infusion of a suspension of catalase-containing particles. In all cases, the ultrasound transducer is positioned over the fluid or tissue or location of interest and used to detect a signal generated by microbubbles. This signal can be used to generate an ultrasound image to visualize the generated microbubbles, where the presence of microbubbles indicates the presence of localized $H_2O_2$. In one embodiment, the catalase-containing material is a coating on an inner surface of a microtube. In another embodiment, the catalase-containing material is one or more layer of catalase coated onto a nanosphere or microsphere, which may be a silica particle. The layers may be alternating layers of catalase and polystyrene sulfonate. In still another embodiment, the catalase-containing material may be an implantable device with a catalase coating, where the device may be a catheter, central venous line, dialysis catheter, temporary inferior vena cava (IVC) filter, surgical implant, peripheral vascular graft material, orthopedic implant, or hernia mesh. In yet another embodiment the catalase-catalase-containing material may be particles that can be administered as a suspension intravenously. If the catalase is contained within the particle, the particle shell is permeable to water and $H_2O_2$. Such material can be silica or hydrogels or the like.

In yet another aspect of the invention, a method is provided to visualize the presence and distribution of low concentrations of hydrogen peroxide ($H_2O_2$) in vivo using ultrasound imaging, by introducing a reacting agent(s) or a catalytic material(s) in vivo to convert $H_2O_2$ into water and oxygen ($O_2$) bubbles. The bubbles can then be visualized using ultrasound imaging devices. The catalytic materials may be packaged in small sizes ranging from 10 nm to 100 microns, depending on the application, or they may be incorporated into a packaging material, either directly into a packaging material having a porous and/or hollow structure, coated onto the surface of the packaging material, or coated onto a surface of an implantable medical device such as a catheter. The surface of the catalytic device, i.e., the packaging material, can itself be formed from catalytic and/or biocatalytic materials. The surface may also be configured to protect the catalytic materials from the environment and/or to control the size of the microbubbles produced.

BRIEF DESCRIPTION OF THE DRAWINGS

FIG. 1A is a diagrammatic view of a first embodiment of a catalytic converter showing production of oxygen; FIG. 1B is an image of microbubble generation produced using light microscopy; FIG. 1C is an image of microbubble generation produced using ultrasound; FIG. 1D is a diagram of the basic experimental set-up; FIG. 1E is a series of ultrasound images generated at different hydrogen peroxide concentrations; FIG. 1F is a plot of hydrogen peroxide concentration versus ultrasound signal intensity.

FIGS. 2A-2L illustrate detection of $H_2O_2$ using catalase-coated silica nanospheres converters (NSCs), where FIG. 2A is a diagrammatic view of an exemplary nanosphere; FIG. 2B is a SEM image of the nanospheres; FIG. 2C is a plot number of particles per batch versus number of layers; FIG. 2D is a plot of catalase activity per batch versus number of layers; FIG. 2E is a plot of catalase per particle versus concentration versus number of layers; FIG. 2F is chart showing detection threshold versus number of layers in saline and plasma; FIG. 2G is a plot of intensity versus $H_2O_2$ concentration; FIG. 2H is a chart showing the range of $H_2O_2$ concentration versus detection threshold; FIG. 2I is a plot of intensity versus $H_2O_2$ concentration for 3 layers with and without PSS; FIG. 2J is a chart showing catalase concentration versus detection threshold; FIG. 2K is a plot of the number of particles versus intensity; and FIG. 2L is a chart showing particle number versus detection threshold.

FIG. 3A is a diagram of the test set-up; FIG. 3B shows images of exemplary neutrophils taken at 40× magnification after Wright staining; FIG. 3C is a scatterplot showing presence of $H_2O_2$ in neutrophils versus intensity; FIG. 3D is a set of photographic images showing microbubbles only in tubes containing activated neutrophils and NSCs; and FIG. 3E is a chart showing normalized intensity with and without catalase.

FIG. 4A shows NSCs and microbubbles post-injection and FIG. 4B shows control nanospheres with no catalase and no post-injection microbubbles.

DETAILED DESCRIPTION

Figure 1A:
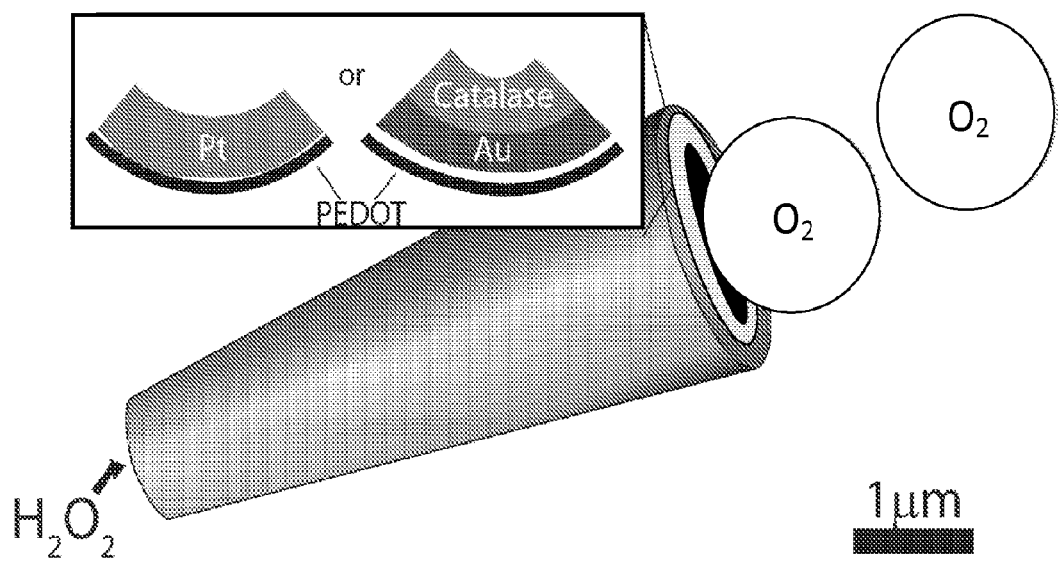
FIGS. 1A-1F illustrate ultrasound-based visualization of oxygen microbubbles where

According to the present invention, oxygen microbubbles formed by nanoconverters can be visualized with ultrasound. FIG. 1D illustrates and exemplary test layout in which a transfer pipette 20 was modified to contain a port 22 through which hydrogen peroxide could be dripped. The pipette 20 was placed in a water bath 10 with transducer 30, which was connected to the ultrasound unit 12. Microbubbles were imaged using a General Electric LOGIQ E9 ultrasound system.

The following detailed description uses a variety of terms to describe the particles having a material adapted to catalyze $H_2O_2$ into water and oxygen microbubbles. Such terms include "catalytic converters", "nanoconverters", "nanorockets", "micromotors" "micromotor converters", "MMCs", and "NSCs". It will be readily apparent to those in the art that each of these alternative terms refers to a micro- or nano-scale particle configured to induce the production of microbubbles in the presence of $H_2O_2$.

Figure 1B:
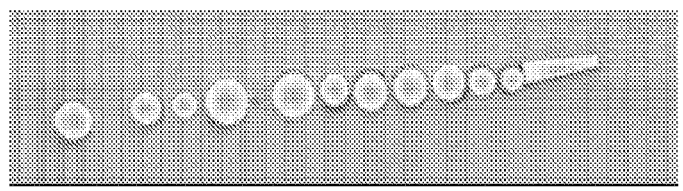
Figure 1C:
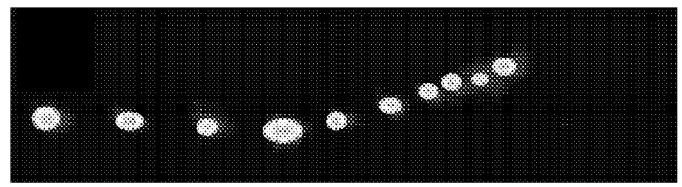
Figure 1D:
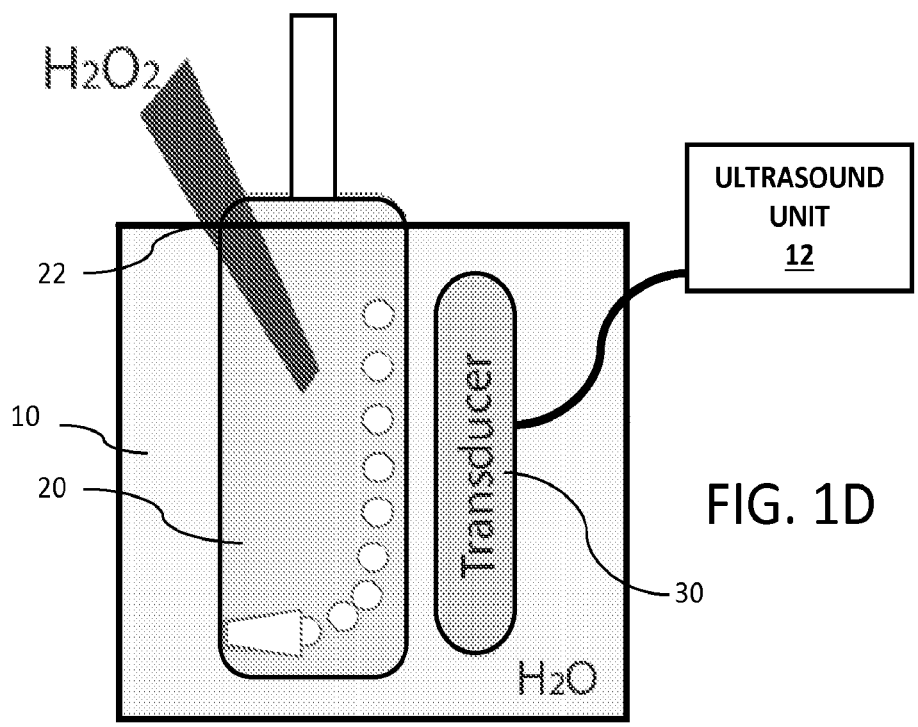

FIGS. 1A-1F illustrate a first evaluation of the inventive method using a catalytic converter referred to as "nanorockets" or "micromotor converters" ("MMCs"). FIG. 1A diagrammatically illustrates the MMCs, which are tubular (truncated conical) nanostructures lined with platinum or catalase over a gold surface, acting as a catalytic surface causing breakdown of $H_2O_2$.

Micromotors were synthesized as described by W. Gao, et al., "Polymer-based tubular microbots: role of composition and preparation", *Nanoscale*, 2012 Apr. 7; 4(7):2447-53. Briefly, tubular micromotors were prepared using a common template-directed electrodeposition protocol. A CYCLOPORE™ polycarbonate membrane, containing 2 µm diameter conical-shaped micropores (Catalog No 7060-2511; Whatman, Ltd., Maidstone, U. K.), was employed as the template. A 75 nm gold film was first sputtered on one side of the porous membrane to serve as working electrode using the Denton DISCOVERY™ 18 (Denton Vacuum, LLC, Moorestown, N.J.). The sputter was performed at room temperature under vacuum of $5 \times 10^{-6}$ Torr, DC power 200 W and flow Ar to 3.1 mT. Rotation speed was 65 and sputter time was 90 s. A platinum wire and an Ag/AgCl electrode with 3M KCl were ultrasounded as counter and reference electrodes, respectively. The membrane was then assembled in a plating cell with an aluminum foil serving as a contact. Poly(3,4-ethylenedioxythiophene) (PEDOT) microtubes were electropolymerized at +0.80 V for a charge of 0.06 C from a plating solution containing 15 mM EDOT, 7.5 mM $KNO_3$ and 100 mM sodium dodecyl sulfate (SDS); subsequently, the inner Pt tube was deposited galvanostatically at –2 mA for 1800 sec from a commercial platinum plating solution (Platinum RTP; Technic Inc, Anaheim, Calif.). The sputtered gold layer was completely removed by hand polishing with 3-4 µm alumina slurry. The membrane was then dissolved in methylene chloride for 10 min to completely release the microtubes. The latter were collected by centrifugation at 6000 rpm for 3 min and washed repeatedly with methylene chloride, followed by ethanol and ultrapure water (18.2 MΩ cm), three times of each, with a 3 min centrifugation following each wash. All microtubes were stored in ultrapure water at room temperature when not in use.

Catalase lined micromotors were synthesized as described by Gao, et al., supra. Briefly, PEDOT microtubes were electropolymerized at +0.80 V for a charge of 0.06 C from a plating solution containing 15 mM EDOT, 7.5 mM $KNO_3$ and 100 mM sodium dodecyl sulfate (SDS); subsequently, the inner gold layer is plated at –0.9 V for 1 C from a commercial gold plating solution (OROTEMP® 24 RTU RACK gold plating solution; Technic, Inc., Cranston, R.I., U.S.). The inner Au layer of the bilayer microtubes was functionalized with a mixed MUA/MCH monolayer. A solution of 2.5 mM MUA and 7.5 mM MCH was prepared in ethanol. The micromotors were incubated in the solution overnight. After rinsing the tubes with ethanol for 5 min, they were transferred to an Eppendorf vial containing a 200 µL PBS buffer (pH 5.5) solution with the coupling agents 1-Ethyl-3-[3-dimethylaminopropyl] carbodiimide hydrochloride (EDC), N-hydroxylsulfosuccinimide (Sulfo-NHS) at 0.4 M and 0.1 M respectively, and the enzyme catalase (2 mg mL$^{-1}$). This incubation was carried out 7 hours at 37° C. and thereafter rinsed with PBS with a pH of 7.4 and SDS 0.05 wt % for 15 min at each step. The micromotors were washed repeatedly by centrifugation at 6000 rpm for 3 min with water for three times to remove extra catalase in solution before testing.

Enzyme activity was determined spectrophotometrically based on the decrease in absorbance of hydrogen peroxide at λ=240 nm, according to an adapted method from the Sigma Enzymatic Assay of Catalase (Sigma, protocol EC 1.11.1.6.) Briefly, 100 µl of particle solution was washed by centrifugation at 8000 rpm for three minutes and re-suspended in 27 µl of PBS pH 7.0 before being added to 773 µl of 11 mM $H_2O_2$ solution prepared in 50 mM PBS. After shaking for 10 seconds, the solution was placed in the 800 µl spectrophotometer cuvette and the decrease in absorbance at 240 nm with time was recorded immediately at 20° C. for 2 min. One unit of catalase is defined as decomposing 1 µmol of $H_2O_2$ per minute at pH 7.0 and 20° C.

FIG. 1B is a photomicrograph of microbubbles visible at 0.2% (v/v), or 65.3 mM, $H_2O_2$ using light microscopy. Microbubbles were first detected by ultrasound when MMCs were exposed to 2-5 mM $H_2O_2$. FIG. 1C provides a parallel image to that of FIG. 1B, but generated at a much lower hydrogen peroxide concentration (0.8 mM) using ultrasound. Note that this image has been cropped, rotated and magnified for comparison. Single microbubbles observed at low $H_2O_2$ concentrations became trails of microbubbles as the hydrogen peroxide concentration increased. At the highest concentrations, echogenic MMCs could be seen traveling in a direction opposite the bubble trail. The microbubbles were visible using both standard ultrasound imaging as well as non-linear imaging, a microbubble-only imaging technique that suppresses all linear tissue signals. The best results were obtained when the highest MMC concentration (27000 MMCs/mL) was exposed to 0.13% (v/v)(42.2 mM) $H_2O_2$. The threshold was lowered further (0.8 mM) when the inner surface of the MMC was coated by catalase. However, because these motors were dense, they settled quickly to the bottom of the container.

Figure 1E:
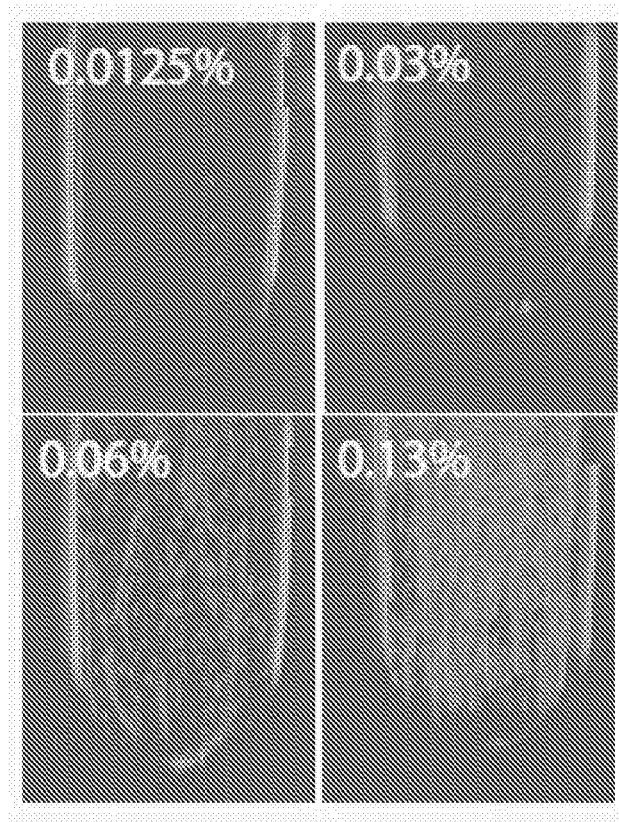
Figure 1F:
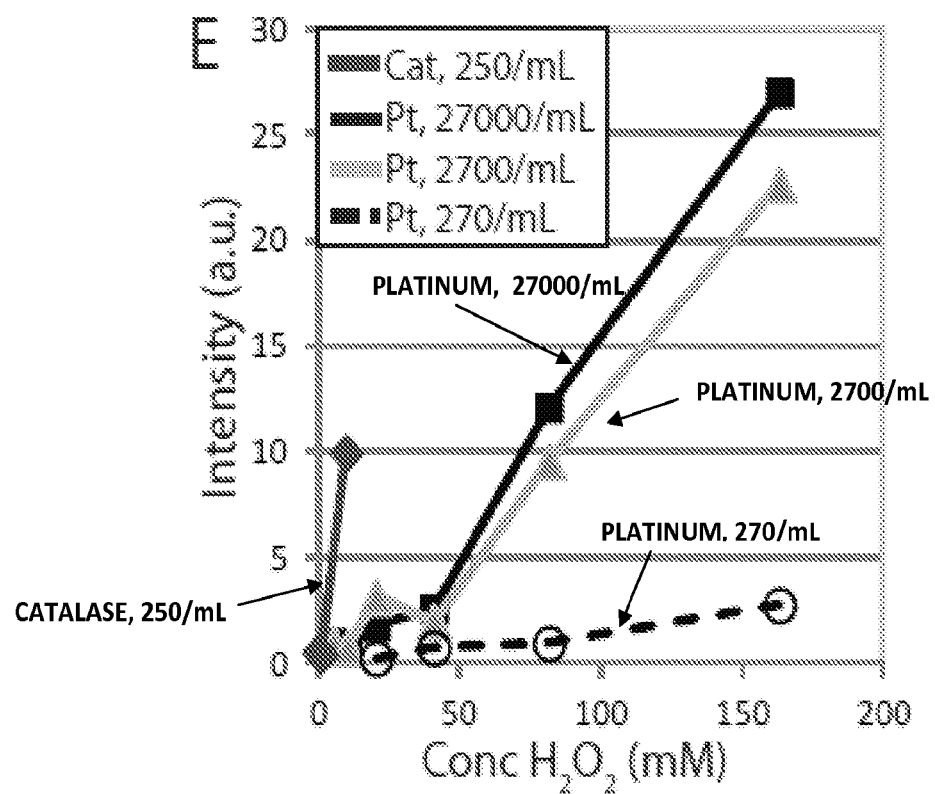

The gross effect of increasing $H_2O_2$ concentration is demonstrated in FIG. 1E. As shown in the upper left image, few microbubbles are visible at 0.0125% (4.1 mM). These were produced by a few MMCs that had settled to the bottom of the container. More MMCs become active and the number of microbubbles increases with increasing $H_2O_2$, as shown by the upper right (0.03%) and lower left (0.06%) images, until a cloud of microbubbles is formed at 0.13% (42.4 mM) $H_2O_2$, as shown in the lower right image. Ovoid regions of interest were drawn and quantitated in FIG. 1F, demonstrating a logarithmic relationship between $H_2O_2$ and ultrasound signal intensity. There is a dose dependence with increasing MMCs as well as significant improvement when the inner surface of the MMC is coated with catalase instead of platinum.

To decrease background echogenicity from hollow motors, decrease the overall size of the nanoconverters and eliminate the metal surface in anticipation of future preclinical testing, stationary $H_2O_2$ nanoconverters (NSCs) were formed by layering concentric shells of catalase and polystyrene sulfonate (sodium polystyrene sulfonate) (PSS) over a 400-500 nm silica sphere, diagrammatically shown in FIG. 2A. This compact spherical design theoretically allows for smaller, less dense particles with biodegradable components that are more suitable for in vivo use.

NSCs were produced using the following process: 1 µl of negatively-charged silicon particles (0.51 µm, Catalog Code SS03N, Sigma-Aldrich) was washed twice by centrifugation for 3 minutes at 8000 rpm, first with B&W&B, then with DI water. Layers of catalase (C3155-50, Sigma-Aldrich) diluted daily into 0.05M PBS, pH 5.0 and a PSS/saline solution (1 mg/mL PSS diluted into 1 mL 0.05M PBS, pH 5.0, containing 29 mg NaCl). Between incubations, particles were washed with 100 µl of DI water by centrifuging at 8000 rpm for three minutes. These steps were repeated to produce the desired number of layers. Particles were re-suspended in either PBS (pH7, Gibco) or HBSS (Gibco) prior to experiments.

Scanning electron microscopy (SEM) confirms the presence of several 400-500 nm particles with uniform spherical shape (FIG. 2B). For all experiments, SEM images were obtained with a Philips XL30 ESEM instrument, using an acceleration potential of 20 kV. Optical images were captured using an inverted optical microscope (Nikon Instrument, Inc. Ti-S/L100) coupled with a 20× objective, a Hamamatsu digital camera C11440 using the NIS-Elements AR 3.2 software.

Figure 2C:
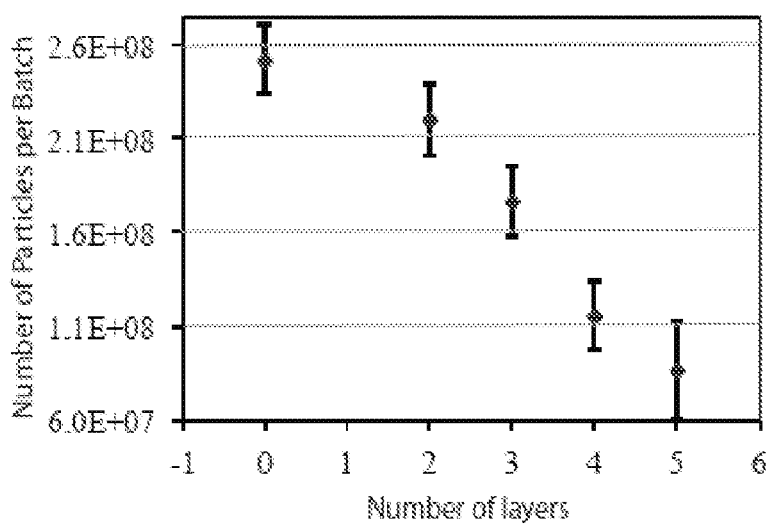
Figure 2D:
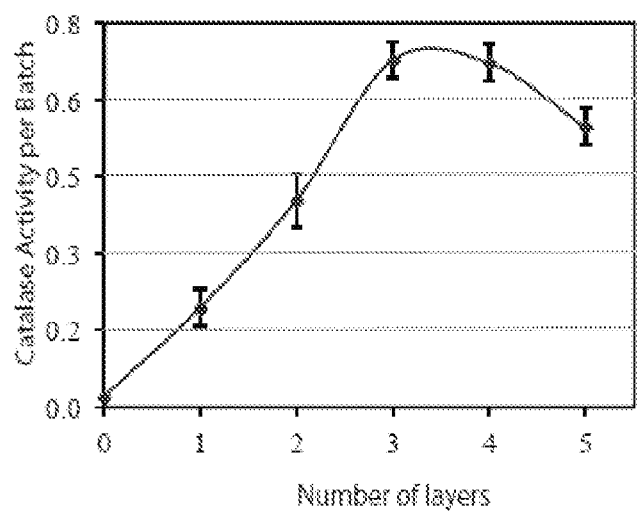
Figure 2E:
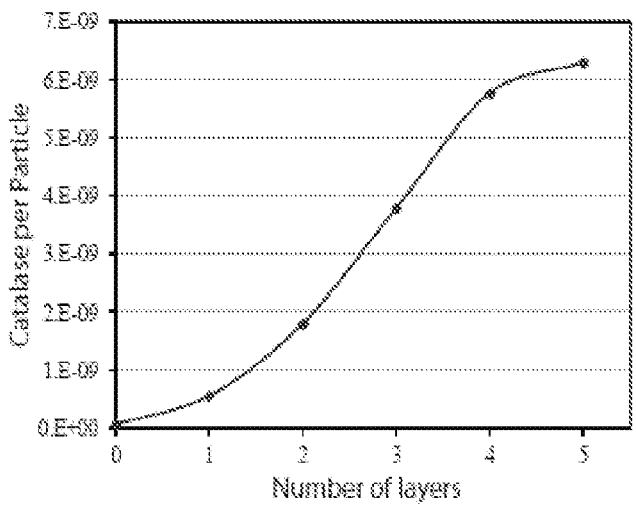

Increasing the number of layers (shells) in the bioactive multilayer decreases the threshold concentration of $H_2O_2$ at which microbubbles are first detected as hydrogen is added slowly to the top of the tube. FIGS. 2C-2E illustrate the moderate decrease in particle number as more layers are added to the bioactive multilayer, possibly due to washing during the manufacturing process. Error bars show standard deviation. As shown by the curve in FIG. 2D, catalase activity associated with the nanospheres increases until three layers are added, then begins to drop off with additional layers. Increasing the number of catalase layers on the outer surface decreases the threshold concentration of $H_2O_2$ at which microbubbles are first detected by ultrasound with minimal improvement seen between 3 and 5 layers. Measurements were repeated three times for three distinct batches of particles. The mean±standard error is shown. The number of spheres is held constant at $1.3 \times 10^7$ ($4.3 \times 10^9$/L.) FIG. 2E confirms that the catalase per particle increases as expected with increasing layers.

Figure 2F:
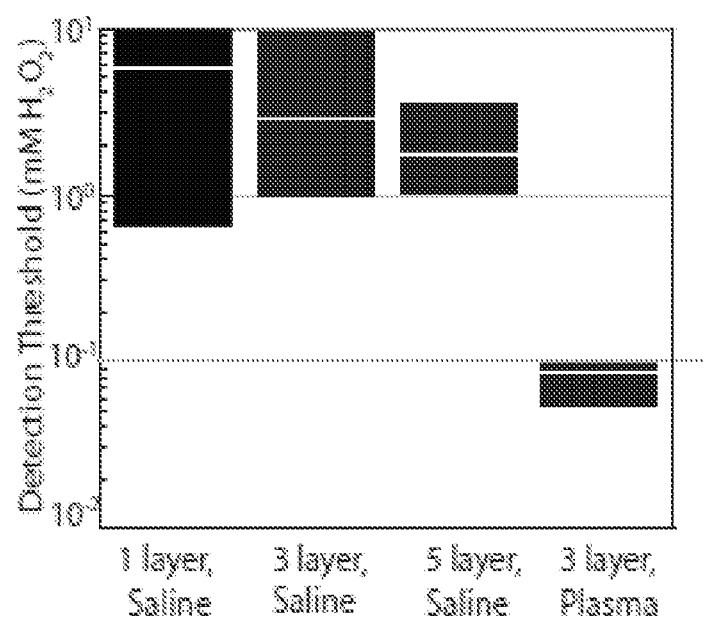
Figure 2G:
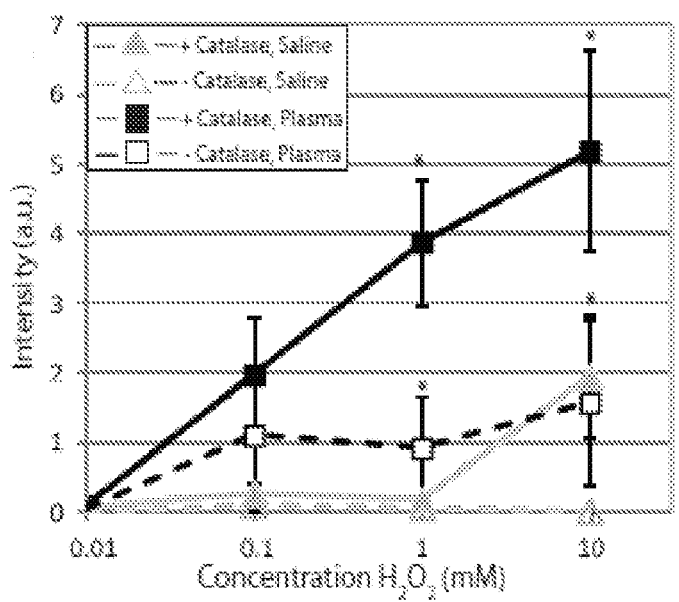

FIGS. 2F and 2G demonstrate that performing the assay in plasma decreases the detection limit compared with buffered saline and sodium hydrate cholate. For all particle geometries, using plasma to suspend the particles instead of a mixture of buffered saline (PBS) and sodium cholate decreased the detection limit by another 10- to 100-fold, possibly due to the presence of lipids and proteins. In FIG. 2F, the black rectangles indicate the range of $H_2O_2$ concentration when microbubbles were first detected by two blinded observers (n=6-8) when $H_2O_2$ is increased incrementally by factors of 10. White lines within the black rectangles indicate the average $H_2O_2$ concentration at which bubbles are first detected for each experiment. The effect of increasing $H_2O_2$ concentration on image intensity is shown in FIG. 2G. Experiments were done in triplicate, and error bars represent standard error of the mean.

Figure 2H:
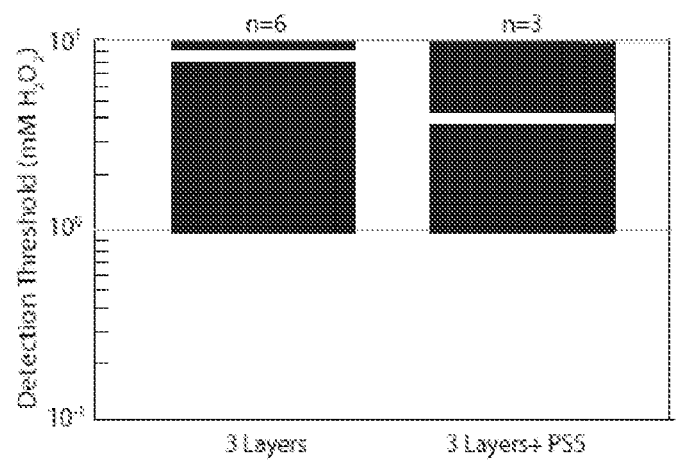
Figure 2I:
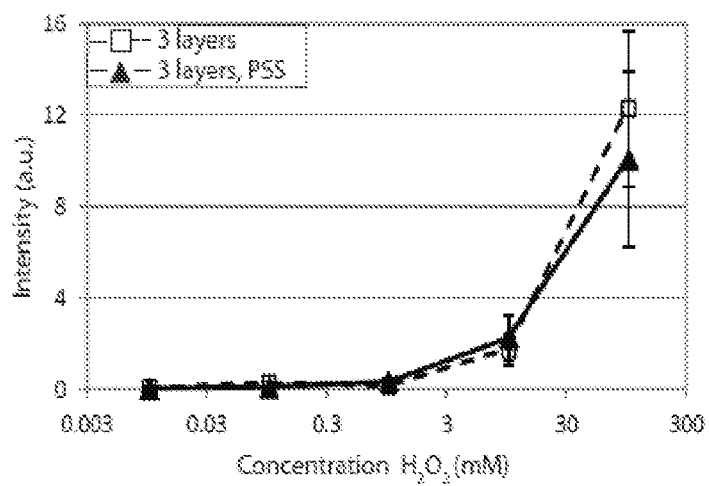

FIGS. 2H and 2I demonstrate that adding an outer layer of polyelectrolyte (PSS) does not significantly change sensitivity to $H_2O_2$, indicating that diffusion through PSS is not rate limiting. The black rectangles and white lines in FIG. 2H correspond to the same features described above relative to FIG. 2F. The effect of increasing $H_2O_2$ concentration on image intensity is shown in FIG. 2I. Experiments were done in triplicate, and error bars represent standard error of the mean.

Figure 2J:
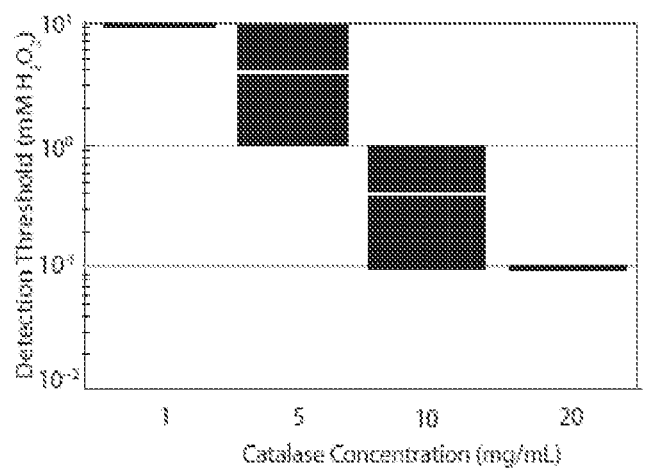

Incorporation of catalase on the NSC surface was more efficient for microbubble formation than was free catalase in solution, since the latter required >5000 U/mL to produce detectable microbubbles. This suggests that sensitivity to $H_2O_2$ may also be affected by other factors in addition to geometry, possibly because the catalase on the surface of the NSCs had a much higher effective concentration, irregularities on the PSS surface eased nucleation, and/or the NSCs themselves acted as nucleation sites upon insonation of the surrounding oxygen saturated fluid. FIG. 2J is a plot of $H_2O_2$ concentration when microbubbles were first detected as a function of free catalase in solution. Experiments were done in triplicate. The black rectangles represent the range of detection thresholds observed; the white lines indicate the average detection threshold.

NSC concentration was determined by diluting the NSCs 100-fold into PBS and injecting the solution into a hemocytometer. The number of particles in a 100 μm³ was counted manually under light microscopy.

Using the experimental set-up shown in FIG. 1D, NSCs at the indicated concentration were placed into a transfer pipette that had been modified to include a port that could be pinned to the back of the water bath for stability. 3 mL phosphate-buffered saline (PBS, Gibco) and 0.04 M sodium hydrate cholate (NaCH, Sigma-Aldrich) were added to the NSCs through the port, and samples were allowed to sit for approximately five minutes. Under ultrasound operating in contrast mode (GE LOGIQ® E9, 6-15 MHz linear transducer, MI<0.20, 14 frames per second), the concentration of hydrogen peroxide was increased incrementally by factors of ten (e.g., 8 μM, 80 μM, 800 μM, . . . ) delivered in low volumes of 3 μL or 30 μL so as to avoid excessive dilution. NSCs were tested side by side with control spheres that did not contain catalase. Detection limits were obtained on the fly by two independent observers blinded to the identity of the tubes. The detection limit was defined as the first point at which characteristic rising bubbles were observed and was recorded at the time of the experiment. All experiments were performed in triplicate.

Stacks of images were analyzed using ImageJ, a public domain, JAVA-based image processing program developed at the National Institutes of Health. An ovoid region of interest was drawn encapsulating the largest area of the tube possible while excluding obvious imaging artifact from the sides of the tube when present. This region was averaged both pre- (3-10 frames) and post- (5-20 frames) administration of $H_2O_2$. Total intensity was defined as the average of the pre-frames subtracted from the average of the post-frames.

Figure 2K:
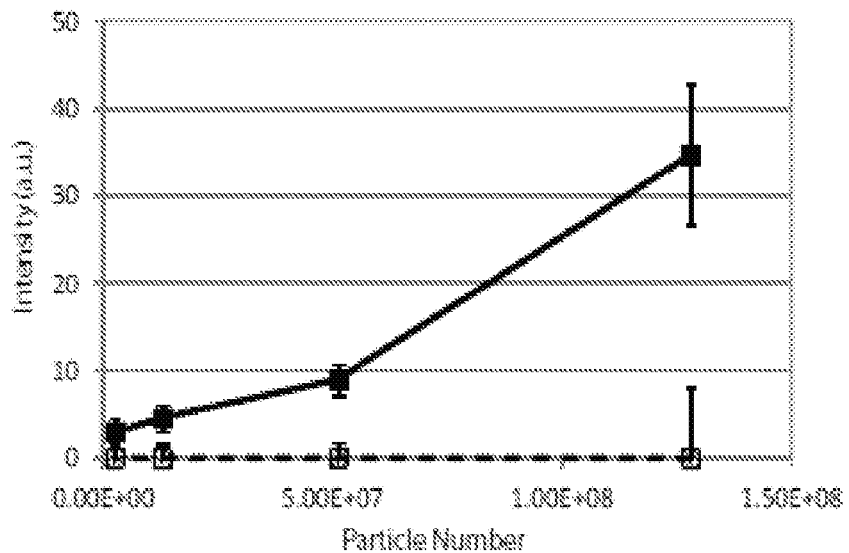
Figure 2L:
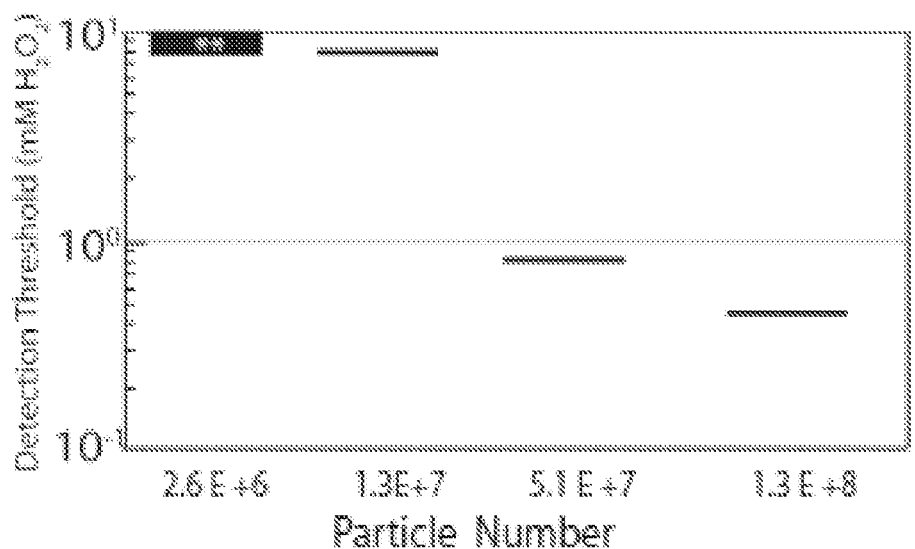

As shown in FIGS. 2K and 2L, increasing the number of NSCs increases ultrasound image intensity from formed microbubbles. FIG. 2K shows image intensity as a function of particle number in suspension when 9.7 mM of $H_2O_2$ is added. Experiments were done in triplicate. Error bars represent the standard error of the mean. FIG. 2L shows the range of $H_2O_2$ concentrations are which microbubbles were detected subjectively when added to four different particle concentrations in saline. The detection threshold could be further decreased by increasing NSC concentration, leading to a final detection threshold as low as 10 μm at a NSC concentration of $4.3 \times 10^6$/mL. At the lowest NSC concentration, microbubbles were detected in only one of the three samples when exposed to 9.7 mM $H_2O_2$.

The three-catalase-layered NSC particles were used for detection of $H_2O_2$ produced during cytotoxic responses in neutrophils triggered by phorbol myristate acetate (PMA). Two methods were used to isolate the neutrophils. For the first method, ammonium chloride preparation, 30 mL of rabbit blood was drawn and spun down at 3000 rcf×15 m. The plasma was removed and frozen. The hematocrit and the buffy coat were incubated in isotonic ammonium chloride buffer (15:1 by volume, 8.32 g/L $NH_4Cl$, 0.84 g/L $NaHCO_3$) for 15-20 minutes. The samples were then spun at 300 rcf for 15 minutes and rinsed twice with HBSS for 10 minutes. Cells were counted with a hemocytometer. The second method used was dextran sedimentation preparation. In this method, 30 mL of rabbit blood was drawn and added to an equal amount of 3% solution of dextran-500 diluted in normal saline. This was allowed incubate at room temperature for approximately 20 minutes, until the hematocrit had settled. Plasma was then removed and centrifuges at 250×g. To reduce the number of red cells present, neutrophils were bathed in 20 mL of ice cold 0.2 saline for exactly 20 seconds. 1.6% saline was then added and the cells were spun for 250 rcf×10 minutes. This was repeated once. A Ficoll gradient was not performed due to time constraints. By Wright stain, these preparations were estimated to be about 50% pure, which is consistent with published studies. Neutrophil activation was accomplished by addition of PMA at 15 ng/mL for one hour.

$H_2O_2$ concentration was assayed using Amplex Red reagent (Life Sciences) using a protocol supplied by the manufacturer. Samples were diluted by 50× prior to use. Samples used for the calibration curve were spiked with non-activated neutrophils to control for the spectral properties of lysed red blood cells contained in the mixture.

Figure 3A:
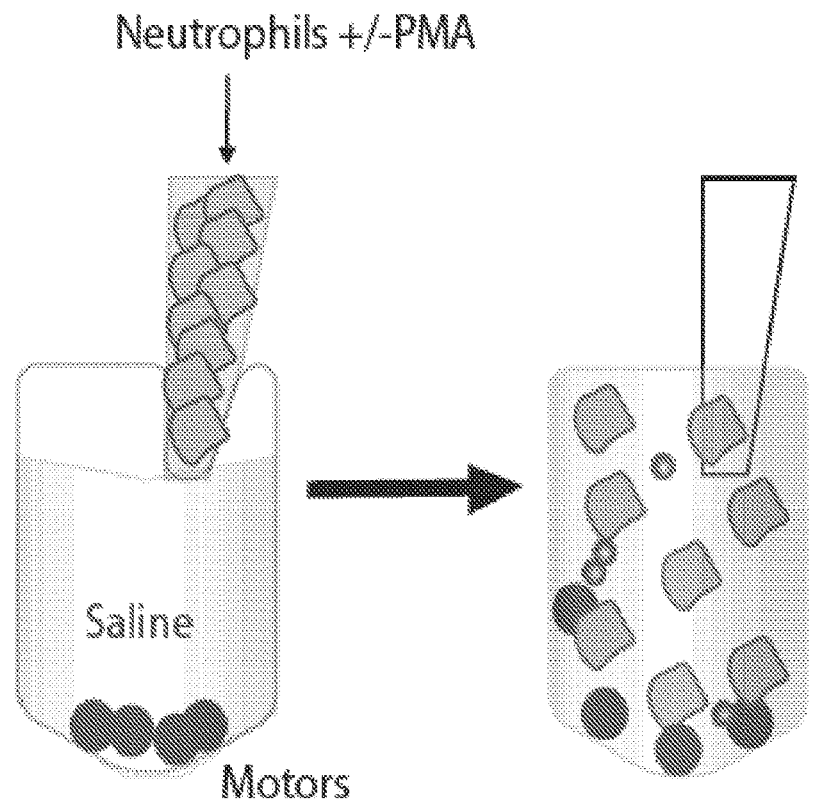
FIGS. 3A-3E illustrate detection of $H_2O_2$ in neutrophil suspensions, where
Figure 3B:
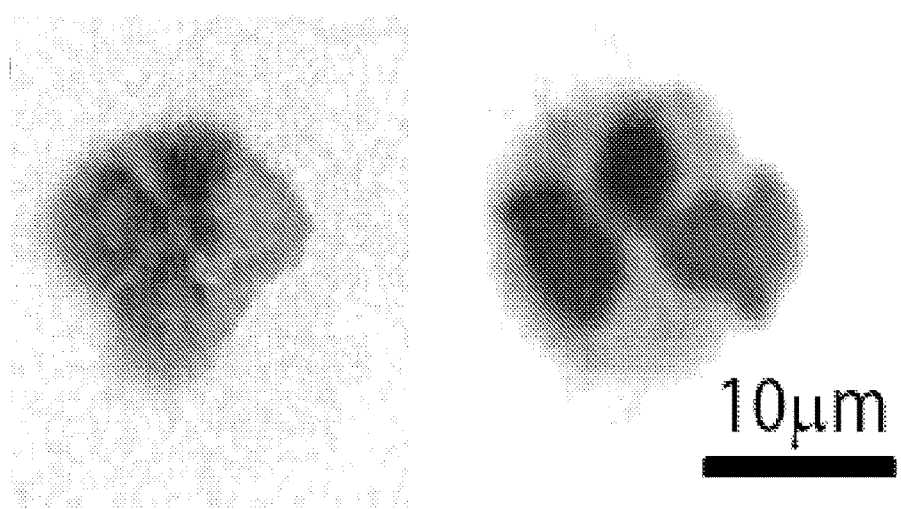
Figure 3C:
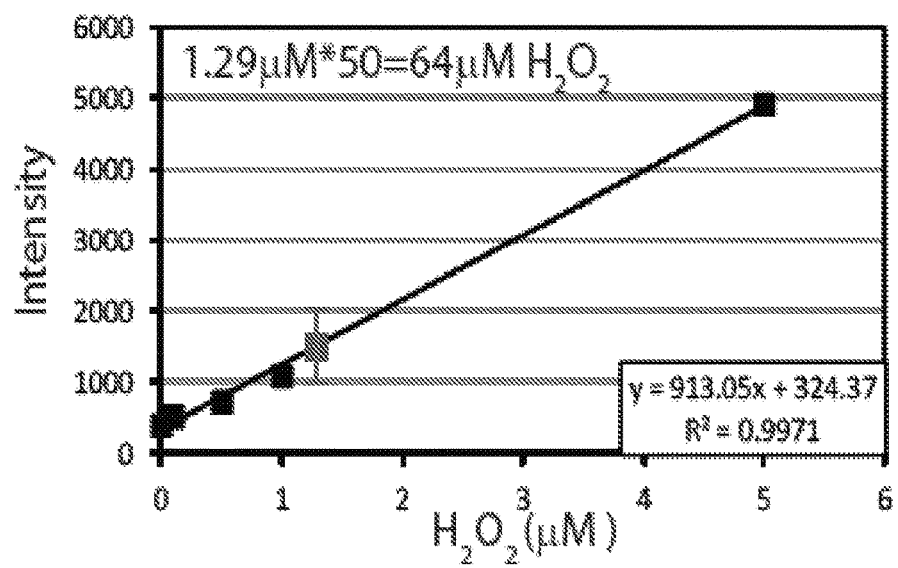
Figure 3D:
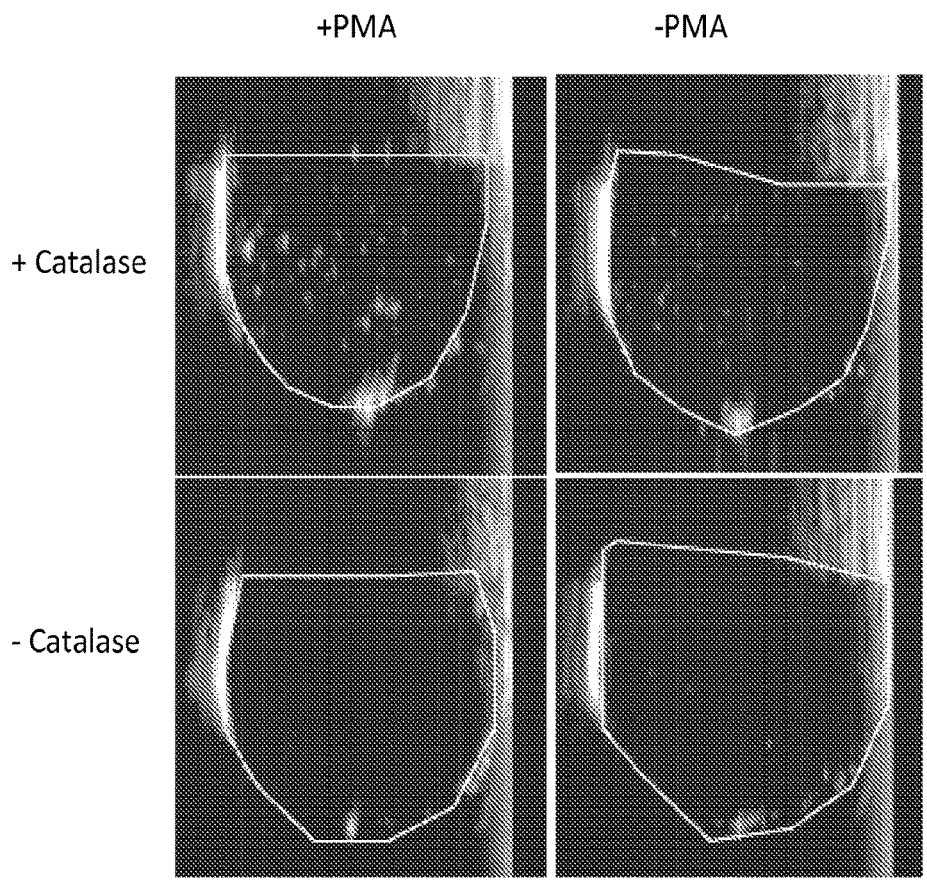

FIG. 3A diagrammatically illustrates the experiment in which neutrophil ($1-3\times10^6$ cells/mL), pre- and post-PMA activation, were added to NSCs and control nanospheres (without catalase) suspended in saline using coded containers. Blind observers rendered judgment as to whether microbubbles were visible on the ultrasound unit display. Both dextran sedimentation and ammonium chloride preparations were used for neutrophil separation in separate experiments, with similar results. Wright staining confirmed the presence of neutrophils (FIG. 3B), and an Amplex red assay for $H_2O_2$ confirmed that the neutrophil-enriched fractions contained 8-60 μM $H_2O_2$ (see FIG. 3C), which is consistent with published data. Neutrophils were counted with a hemocytometer and added to NSCs, or similar control nanospheres without catalase, suspended in saline for a final cell concentration of $1-3\times10^6$ cells/mL. Subjective analysis of the real-time ultrasound was made at the time of the experiment by two blinded observers when the PMA-activated or naïve neutrophils were added to NSCs in each of the three experiments. 25 μL ($1.3\times10^7$) or 250 μL ($1.3\times10^8$) nanospheres were placed into each tube along with 800 μL of saline. Neutrophils were added to a concentration of $1\times10^6$ cells per mL (typically ~100-200 μL). Images were assessed for bubble formation at the time of the experiment by both observers, and preliminary results were documented while still blinded. The test results are shown in FIG. 3D. Microbubbles were observed only when activated neutrophils were added to NSCs. Both $1.3\times10^7$ and $1.3\times10^8$ particles/mL yielded ultrasound-detectable microbubbles, although more microbubbles were seen at the higher concentration.

Figure 3E:
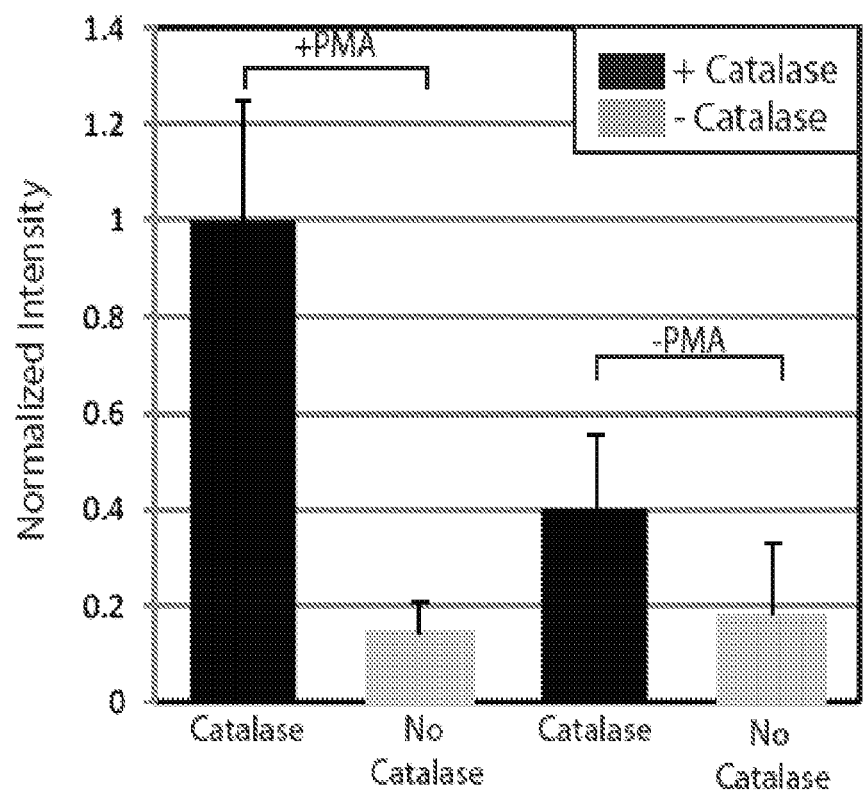

As in the preceding experiments, images were processed using ImageJ. The quantification of video intensity within a region of interest drawn over the lumen of the container was averaged over 20 frames prior to injection. Depending on the experiment, the first 80-200 frames after the addition of neutrophils were ignored to eliminate the possibility of erroneously-introduced microbubbles. Up to 30 frames were collected and again averaged. Frames in which tube movement caused obvious artifacts to appear in the region of interest were eliminated prior to averaging. Intensities of "pre"-images were subtracted from intensities of "post"-images to provide net intensity. FIG. 3E shows the results of a representative experiment done in triplicate, confirming the subjective assessment. Similar results were observed in each of four other experiments, each done in triplicate.

Figure 4A:
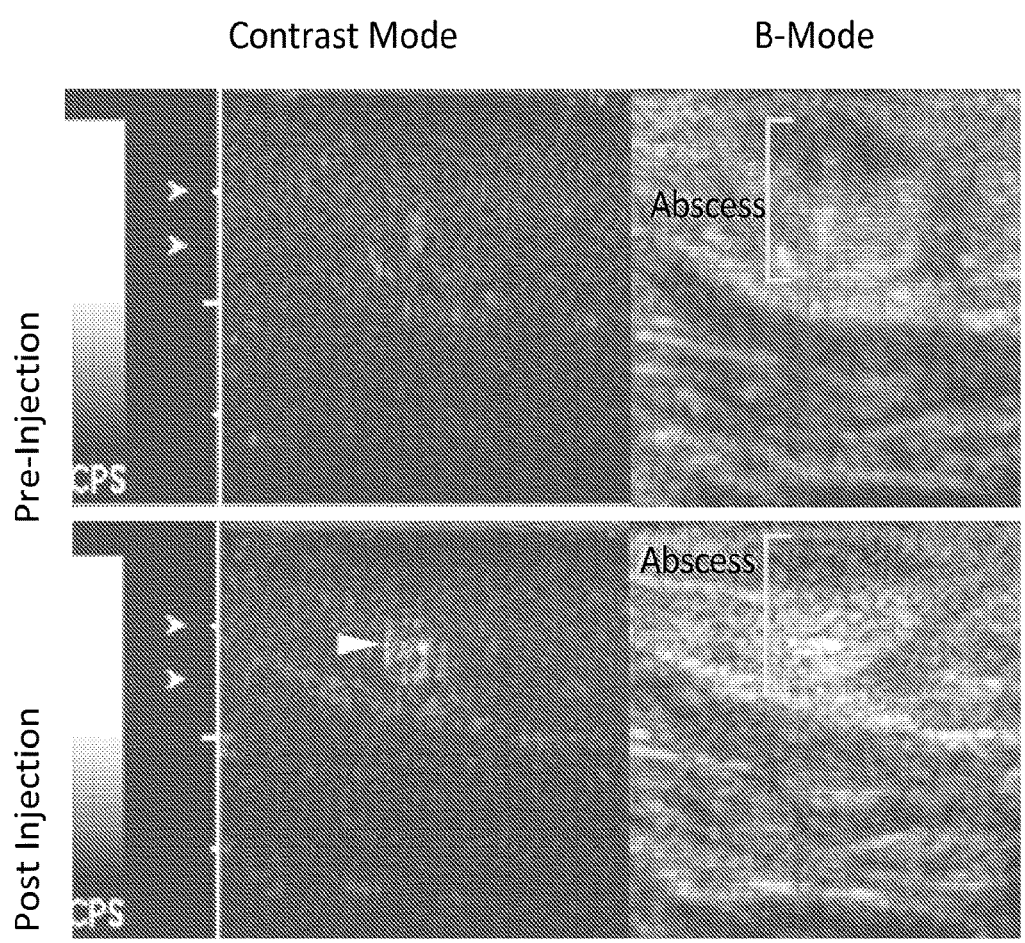
FIGS. 4A-4B are contrast-mode ultrasound images pre- and post-injection of nanospheres into abscesses in a model animal, where
Figure 4B:
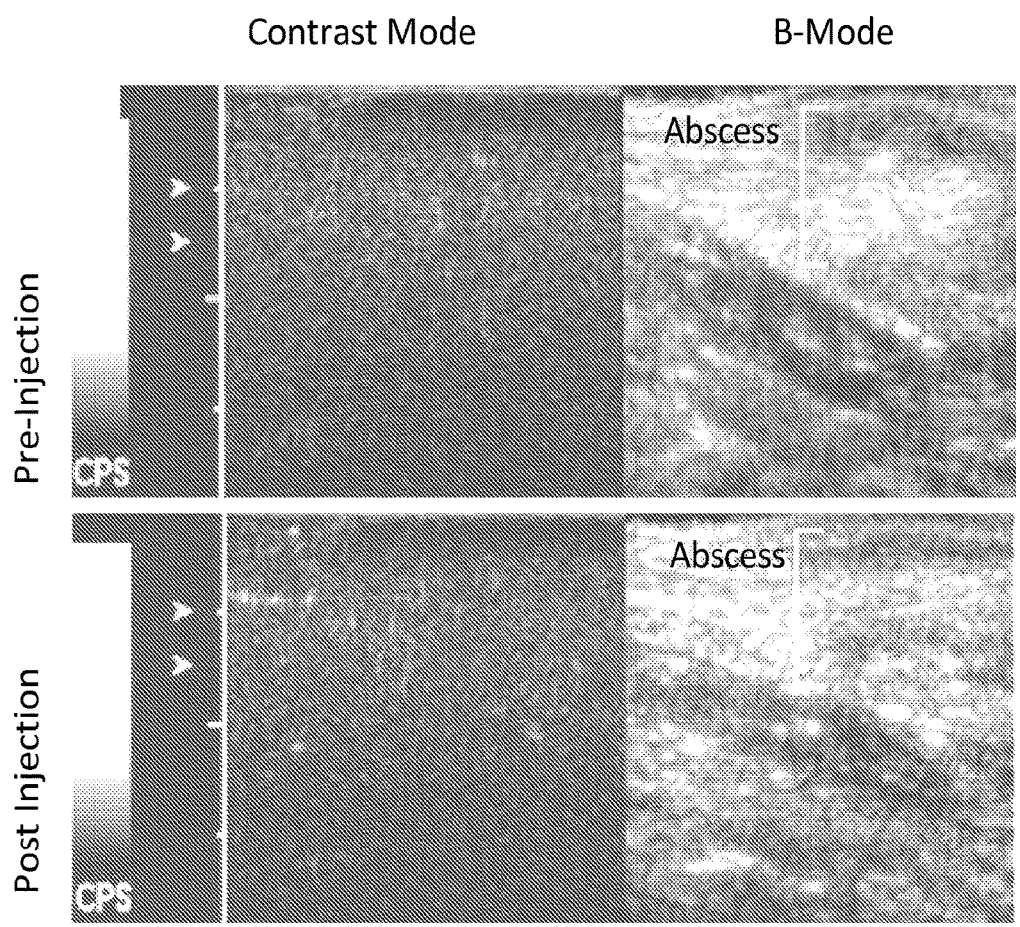

NSCs were tested in an in vivo model of abscess in three eight to ten-month-old Sprague Dawley rats (Harlan Laboratories). Abscesses are characterized by the presence of a large number of neutrophils that release $H_2O_2$ as a response to bacterial invasion. Methicillin-sensitive *Staphylococcus aureus* (MSSA) was grown in LB media (Sigma-Aldrich) at 37° C. until reaching mid-log growth phase as determined by serial $OD_{600nm}$ measurements. Bacteria were then pelleted and re-suspended in 400 μL LB. 25 μL of the re-suspension (corresponding to $6\times10^8$ colony-forming units (CFU), determined retrospectively by plating dilutions onto agar plates) was injected into the right lateral thigh of each animal. Animal vital signs and abscess formation were monitored for each rat over the subsequent four days by visual examination and ultrasound. When ultrasound-detectable abscesses had formed, the animals were anesthetized for nanosphere injections using 1% isofluorane in oxygen. Ultrasound imaging was performed using the 15L8 S transducer of a SEQUOIA® 512 ultrasound system (Siemens Medical Solutions, Mountain View, Calif.) operating at 7.0 MHz, MI=0.18, 16 frames/sec using the CPS microbubble-specific imaging mode. Ultrasound images acquired in real-time from before and for several minutes after nanosphere injection were digitally recorded. First, the control nanospheres ($8\times10^5$ particles suspended in 50 μL PBS) were injected into the abscess margin until ultrasound guidance and the needled withdrawn. Using a different needle, NSCs were injected at the same site 5-10 minutes later. Immediately after injection with NSCs, an echogenic focus formed at the injection site, which was best seen using the contrast-specific imaging technique (B-mode (brightness-mode), also known as "2D mode"), shown in FIG. 4A. A corresponding focus was not seen where control nanospheres were injected (FIG. 4B).

Recorded ultrasound frames were analyzed using ImageJ. Four frames taken prior to NSC injection were averaged as the "pre". Eighty frames taken when movements from the injection subsided were averaged as "post". The "pre" images were subtracted from the "post" images for both control and catalase-containing NSCs in each of the animals and significance was assessed using a Wilcoxon rank sum test, with n=4, U=16, p=0.02. The results suggests that the signal seen at the site of the NSC injection was due to production of oxygen microbubbles in the presence of $H_2O_2$.

Capsuled catalase combined with ultrasound scanning can be used to detect and image elevated $H_2O_2$ locations in vivo for diagnosis and/or real time monitoring of many pathologies and body's response to external perturbations, such as inflammation, cancer, arthritis; detect and image metabolites that can be converted to hydrogen peroxide; and to fuel oxygen requirements for physiologic reactions, among other applications.

Relative to the existing methods of $H_2O_2$ detection, the inventive method provides a number of advantages including detection and imaging $H_2O_2$ in deep tissue (up to 33 cm deep) in vivo; generation of real-time images with high spatial resolution; relatively non-toxic; and readily detected with standard, commercially available ultrasound imagers.

While the foregoing example of in vivo $H_2O_2$ detection was performed using direct injection of capsulated catalase into the infection site, alternative methods for introducing the catalase include suspending catalase-containing particles (nanospheres or microspheres), such as those previously described, in an appropriate fluid for intravenous injection or infusion. The particles may having one or more catalase layers on their exterior surfaces, or they may be formed from a material having a porous or hollow structure so that the catalase may be incorporated into the body of the particle and/or surrounded by a protective shell. Pores or openings in the particle body or shell permit $H_2O_2$ to access the catalase while protecting the catalase from the environment. The intravenous approach provides means for identifying an infection/inflammation when the exact site is not known, or if multiple potential sites may be affected.

Figure 5:
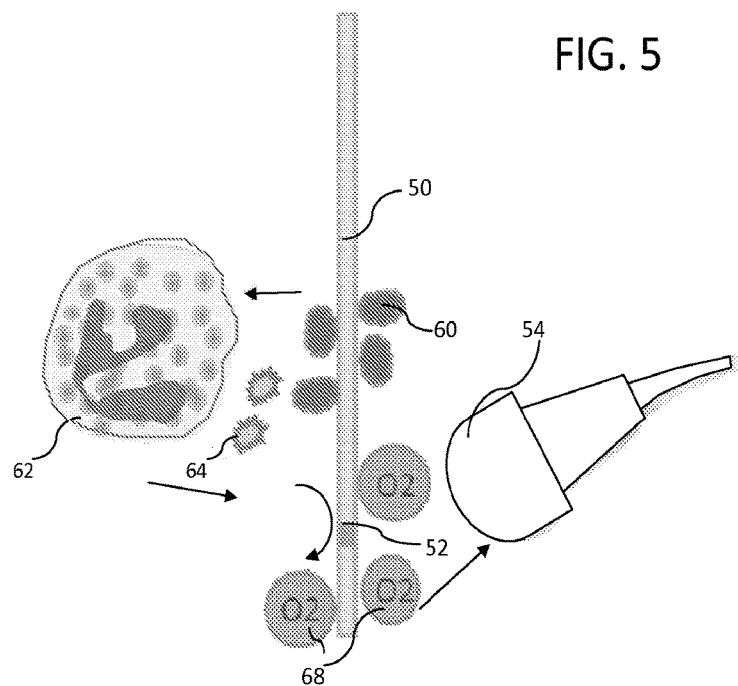
FIG. 5 is a diagrammatic image of a system for in vivo detection of infection using ultrasound imaging.

An important practical application of the inventive technology is for detection of infection at the location of implanted devices such as catheters or prosthetic devices. In this application of the invention, the surface of an implantable device is coated with a high-density catalase prior to implantation. The catalase may be packaged inside thin-walled cellulose tubing, a water-permeable hydrogel, or other biocompatible coating material. Packaging aids in preservation of enzymatic function in a potentially hostile biological environment and protects the patient from potential toxicity. The coating should be sufficiently porous to allow the $H_2O_2$ to access the catalyst while keeping larger, potentially destructive molecules out. Using the example of a catheter, as shown in FIG. 5, catheter 50 with catalase coating 52 is implanted. At some point after implantation, if bacteria 60 appear at the implant site, a respiratory burst from neutrophil 62 is triggered, releasing $H_2O_2$ 64 to attack the bacteria. When the $H_2O_2$ comes into contact with the catalase 52, oxygen microbubbles 68 are produced. Ultrasound transducer 54 is positioned so that it can generate an image of the catheter 50 and the microbubbles 68 that were produced by catalysis of the $H_2O_2$.

Figure 6:
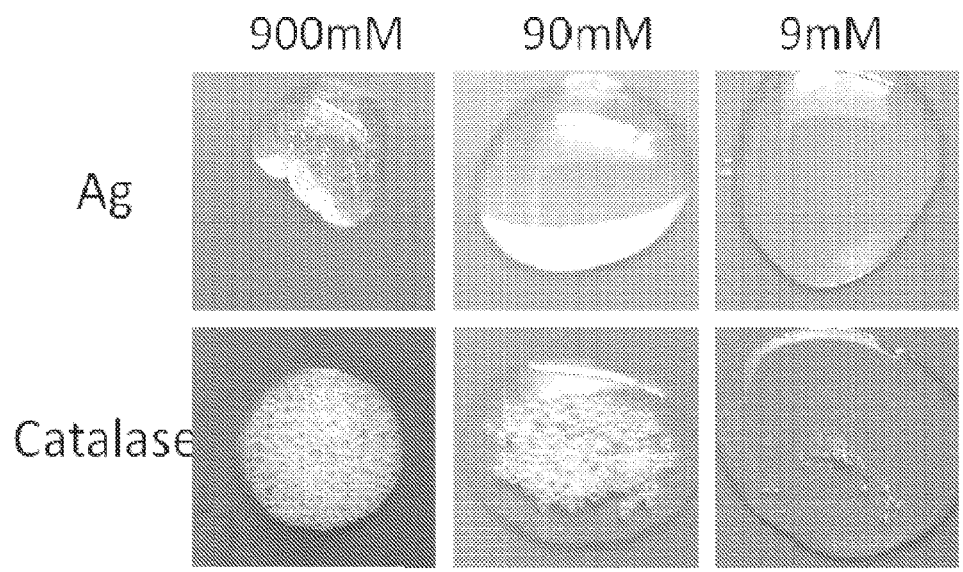
FIG. 6 is a series of photographs comparing microbubble production on a plain metal surface and catalase-coated surface at different concentrations of $H_2O_2$.

FIG. 6 provides photographic images of drops of $H_2O_2$ at different concentrations, 900 mM, 90 mM, and 9 mM on slides. The upper images show the $H_2O_2$ on silver slides. The slides in the lower images were coated with concentrated catalase. As is apparent from the images, catalase dried on the slide creates visibly-detectable (large) bubbles when overlaid with relatively low concentrations of $H_2O_2$. Ultrasound-detectable microbubbles are detectable from catalase-coated microspheres at $H_2O_2$ concentrations as low as 50-100 µM, which is similar to the level of hydrogen peroxide detected clinically in urine from infected patients. This demonstrates the additional application of the invention for in vitro detection of localized hydrogen peroxide in a fluid sample extracted from a patient, e.g., urine, pus, or liquid removed from a mass, and may be used as a quick test for the presence of oxidative stress.

The inventive detection strategy can be utilized in conjunction with Foley catheters, temporary and permanent central venous lines, dialysis catheters, temporary IVC filters, surgical implants such as peripheral vascular graft material, orthopedic implants or hernia mesh. In each case, the invention has the potential for avoiding the surgical removal of expensive implants if the infection site is elsewhere.

REFERENCES

1. Stone, J. R., An assessment of proposed mechanisms for sensing hydrogen peroxide in mammalian systems. *Arch Biochem Biophys*, 2004. 422(2): p. 119-24.
2. Szatrowski, T. P. and C. F. Nathan, Production of large amounts of hydrogen peroxide by human tumor cells. *Cancer Res*, 1991. 51(3): p. 794-8.
3. Cai, H., K. K. Griendling, and D. G. Harrison, The vascular NAD(P)H oxidases as therapeutic targets in cardiovascular diseases. *Trends Pharmacol Sci*, 2003. 24(9): p. 471-8.
4. Gius, D. and D. R. Spitz, Redox signaling in cancer biology. *Antioxid Redox Signal*, 2006. 8(7-8): p. 1249-52.
5. Test, S. T. and S. J. Weiss, Quantitative and temporal characterization of the extracellular $H_2O_2$ pool generated by human neutrophils. *J Biol Chem*, 1984. 259(1): p. 399-405.
6. Wang, J., Can man-made nanomachines compete with nature biomotors? *ACS Nano*, 2009. 3(1): p. 4-9.
7. Mallouk, T. E. and A. Sen, Powering nanorobots. *Sci Am*, 2009. 300(5): p. 72-7.
8. Gao, W., et al., Highly Efficient Catalytic Microengines: Template Electrosynthesis of Polyaniline/Platinum Microtubes. *Journal of the American Chemical Society*, 2011. 133(31): p. 11862-11864.
9. Lee, D., et al., In vivo imaging of hydrogen peroxide with chemiluminescent nanoparticles. *Nat Mater*, 2007. 6(10): p. 765-769.
10. Lippert, A. R., et al., A Hydrogen Peroxide-Responsive Hyperpolarized 13C MRI Contrast Agent. *Journal of the American Chemical Society*, 2011. 133(11): p. 3776-3779.
11. Gao, W., S. Sattayasamitsathit, and J. Wang, Catalytically propelled micro-/nanomotors: how fast can they move? *Chem Rec*, 2012. 12(1): p. 224-31.
12. Gao, W., et al., Polymer-based tubular microbots: role of composition and preparation. *Nanoscale*, 2012. 4(7): p. 2447-53.
13. Eggleton, P., R. Gargan, and D. Fisher, Rapid method for the isolation of neutrophils in high yield without the use of dextran or density gradient polymers. *J Immunol Methods*, 1989. 121(1): p. 105-13.

The invention claimed is:

1. A method for detection of localized hydrogen peroxide, comprising:
    introducing at least one object having a catalase coating into a location of interest in which an inflammatory response is suspected, the catalase coating adapted for catalyzing hydrogen peroxide within the location of interest into oxygen microbubbles;
    positioning an ultrasound transducer over the location of interest; and
    generating and detecting an ultrasound signal to generate an image therefrom, wherein the presence of oxygen microbubbles within the image indicates the presence of localized hydrogen peroxide within the location of interest.

2. The method of claim 1, wherein the at least one object is a microtube and the catalase coating is disposed on an inner surface of the microtube.

3. The method of claim 1, wherein the at least one object is a plurality of nanospheres or microspheres having pores or openings therein and the catalase coating is disposed at least within the pores or openings.

4. The method of claim 3, wherein each of the plurality of nanospheres or microspheres further comprises a shell adapted to permit the entry of hydrogen peroxide to interact with the catalase.

5. The method of claim 1, wherein the at least one object is a silica particle having one or more layers of the catalase coating disposed on an outer surface of the silica particle.

6. The method of claim 5, wherein the one or more layers of the catalase coating are alternated with layers of polystyrene sulfonate.

7. The method of claim 1, wherein the at least one object is an implantable medical device, wherein the catalase is coated onto a surface of the implantable medical device.

8. The method of claim 7, wherein the catalase coating is a first coating, and wherein the implantable medical device further comprises a second coating, wherein the second coating is protective.

9. The method of claim 8, wherein the second coating is a cellulose tubing.

10. The method of claim 8, wherein the second coating is a water-permeable hydrogel.

11. The method of claim 7, wherein the implantable medical device is selected from the group consisting of catheters, central venous lines, dialysis catheters, temporary inferior vena cava (IVC) filters, surgical implants, peripheral vascular graft material, orthopedic implants, and hernia mesh.

12. The method of claim 1, wherein the step of generating an ultrasound image comprises generating a B-mode image.

13. The method of claim 1, wherein the location of interest is an in vitro fluid sample from a patient.

14. The method of claim 1, wherein the location of interest is a tissue site in a live subject.

15. The method of claim 14, wherein the step of introducing is selected from the group consisting of percutaneous injection, intravenous injection, intravenous infusion, implantation of the at least one object, and insertion of the at least one object through a body orifice.

16. A system for detecting localized hydrogen peroxide, comprising:
 at least one object having a surface with a catalase-containing coating configured for introduction into a location of interest in which an inflammatory response is suspected, the catalase adapted for catalyzing hydrogen peroxide within the location of interest into oxygen microbubbles;
 an ultrasound transducer; and
 an ultrasound imaging system for detecting oxygen microbubbles generated by catalysis of the hydrogen peroxide at the location of interest.

17. The system of claim 16, wherein the at least one object is a microtube and the catalase-containing coating is disposed on an inner surface of the microtube.

18. The system of claim 16, wherein the at least one object is a plurality of nanospheres or microspheres having pores or openings therein and the catalase-containing coating is disposed at least within the pores or openings.

19. The system of claim 18, wherein the plurality of nanospheres or microspheres are suspended in a fluid.

20. The system of claim 16, wherein the at least one object is a silica particle having a plurality of alternating layers of catalase and polystyrene sulfonate disposed on an outer surface of the silica particle.

21. The system of claim 16, wherein the at least one object is an implantable medical device.

22. The system of claim 21, wherein the catalase-containing coating is a first coating, and wherein the implantable medical device comprises a second coating, wherein the second coating is protective.

23. The system of claim 22, wherein the second coating is a cellulose tubing.

24. The system of claim 22, wherein the second coating is a water-permeable hydrogel.

25. The system of claim 21, wherein the implantable medical device is selected from the group consisting of catheters, central venous lines, dialysis catheters, temporary inferior vena cava (IVC) filters, surgical implants, peripheral vascular graft material, orthopedic implants, and hernia mesh.

26. The system of claim 16, wherein the ultrasound imaging system is configured to operate in B-mode.

27. The system of claim 16, wherein the location of interest is an in vitro fluid sample from a patient.

28. The system of claim 16, wherein the location of interest is a tissue site in a live subject.

* * * * *